(12) United States Patent
Wasner et al.

(10) Patent No.: US 7,321,802 B2
(45) Date of Patent: Jan. 22, 2008

(54) PROCESS FOR SETTING AN ANESTHESIA APPARATUS OR RESPIRATOR

(75) Inventors: Carsten Wasner, Techau (DE); Hubertus Koch, Lübeck (DE); Franz Urbanski, Lübeck (DE)

(73) Assignee: Dräger Medical AG & Co. KGaA (DE)

( * ) Notice: Subject to any disclaimer, the term of this patent is extended or adjusted under 35 U.S.C. 154(b) by 318 days.

(21) Appl. No.: 11/120,347

(22) Filed: May 2, 2005

(65) Prior Publication Data

US 2006/0021619 A1    Feb. 2, 2006

(30) Foreign Application Priority Data

Jul. 29, 2004    (DE)    ...................... 10 2004 036 879

(51) Int. Cl.
*G06F 17/00*    (2006.01)

(52) U.S. Cl. .............................. 700/90; 700/1; 700/83; 128/204.21

(58) Field of Classification Search ................ 700/300, 700/1, 83, 90, 299; 128/204.21, 204.18, 128/204.23, 200.24, 203.25, 205.21; 200/400, 200/412; 345/184
See application file for complete search history.

(56) References Cited

U.S. PATENT DOCUMENTS

| | | | | | |
|---|---|---|---|---|---|
| 5,598,838 | A | * | 2/1997 | Servidio et al. | 128/204.23 |
| 5,678,539 | A | * | 10/1997 | Schubert et al. | 128/204.21 |
| 5,862,802 | A | * | 1/1999 | Bird | 128/204.18 |
| 5,986,495 | A | * | 11/1999 | Chen | 327/447 |
| 6,188,407 | B1 | * | 2/2001 | Smith et al. | 715/841 |
| 6,305,372 | B1 | * | 10/2001 | Servidio | 128/204.21 |
| 7,038,667 | B1 | * | 5/2006 | Vassallo et al. | 345/184 |
| 2001/0027791 | A1 | * | 10/2001 | Wallace et al. | 128/204.21 |
| 2002/0099477 | A1 | * | 7/2002 | Wallace et al. | 700/299 |
| 2004/0097844 | A1 | * | 5/2004 | Van Brunt et al. | 601/41 |
| 2004/0118404 | A1 | * | 6/2004 | Wallace et al. | 128/205.23 |
| 2004/0154910 | A1 | * | 8/2004 | Hayashi | 200/412 |

FOREIGN PATENT DOCUMENTS

DE    195 00 529 C2    8/1996

* cited by examiner

*Primary Examiner*—Leo Picard
*Assistant Examiner*—Carlos Ortiz-Rodriguez
(74) *Attorney, Agent, or Firm*—McGlew & Tuttle P.C.

(57) ABSTRACT

A process for setting an anesthesia apparatus or respirator with a control unit controlling the respiration is wherein a) after selecting an input sector for a respiration parameter by pressing the rotary and acknowledge switch and keeping it pressed beyond a preset first time threshold and by subsequently adjusting same corresponding to the direction of rotation of the rotary and acknowledge switch, an increase or decrease in the value of the selected parameter is brought about directly via the control unit, b) the set value of the selected parameter is changed over into the presetting by releasing the rotary and acknowledge switch, c) repeated pressing of the rotary and acknowledge switch and keeping it pressed within a second preset time threshold after releasing the rotary and acknowledge switch according to b) leads to the setting of the parameter selected with an increased or decreased value according to a), so that a further adjustment of the selected parameter setting is possible, d) pressing and releasing the rotary and acknowledge switch within the first time threshold after one of the steps a) or b) brings about the confirmation of the set parameter setting.

19 Claims, 1 Drawing Sheet

PROCESS FOR SETTING AN ANESTHESIA APPARATUS OR RESPIRATOR

CROSS REFERENCE TO RELATED APPLICATIONS

This application claims the benefit of priority under 35 U.S.C. § 119 of German Application DE 10 2004 036 879.1 filed Jul. 29, 2004, the entire contents of which are incorporated herein by reference.

FIELD OF THE INVENTION

The present invention pertains to a process for setting an anesthesia apparatus or respirator (ventilator) by means of an input unit for the input of commands into a control unit controlling the respiration, wherein the input unit is combined with a display unit.

BACKGROUND OF THE INVENTION

A control unit for a respirator as well as a process with the features of the type described in the introduction are disclosed in DE 195 00 529 C2. The patients connected to an anesthesia apparatus or respirator (ventilator) are respirated (ventilated) by means of respiration systems which are known per se, which are described as an example in the publication. Furthermore, it is known from this publication that respiration parameters or selected forms of respiration can be entered via input sectors of a touch-sensitive flat screen and the parameters to be changed can be switched by touching the corresponding input sector in a functional connection with the input element. The value of the corresponding parameter can then be changed numerically by means of the input element. The input element is preferably designed as a combined rotary and acknowledge switch. By actuating the acknowledge switch, which is likewise switched into functional connection with the input sector on touching, an acknowledge function is activated, and the respiration parameter to be reset is taken over into the control unit as a new set value only thereafter. The acknowledge function is triggered by pressing the rotary and acknowledge switch.

One drawback of the prior-art setting process arises from the fact that the respiration parameter set becomes effective in the respiration control via the control unit only with the confirmation. This setting operation represents a limitation in case of clinical maneuvers to be performed manually, in which the person operating the apparatus wants to perform operating steps following each other rapidly or adjust an optimal respiration setting during the adjustment by observing the patient.

SUMMARY OF THE INVENTION

Thus, the object of the present invention is to improve the prior-art process in order to integrate a plurality of individual setting operations during the respiration and thus also to make possible continuous clinical respiration maneuvers without loss of time.

According to the invention, a process is provided for setting an anesthesia apparatus or respirator by means of an input unit for the input of commands into a control unit controlling the respiration. The input unit is combined with a display unit wherein the input unit has a keyboard for activating preselected input sectors as well as associated output sectors for respiration parameters and the corresponding value of the parameters. The input unit is provided with a combined rotary and acknowledge switch, which is in functional connection with the input sectors. After selecting an input sector for a respiration parameter by pressing the rotary and acknowledge switch and keeping it pressed beyond a preset first time threshold and by subsequently adjusting it corresponding to the direction of rotation of the rotary and acknowledge switch, an increase or decrease of the value of the selected parameter is brought about directly via the control unit. A change-over of the set value of the selected parameter into the presetting takes place by releasing the rotary and acknowledge switch. Repeated pressing of the rotary and acknowledge switch and keeping it pressed within a second, preset time threshold after releasing the rotary and acknowledge switch leads to the setting of the parameter selected with an increased or decreased value, so that a further adjustment of the selected parameter setting is possible. Pressing the rotary and acknowledge switch and keeping it pressed within a first time threshold after selecting or change-over brings about confirmation of the set parameter setting.

The selected respiration parameter may be the inspiratory pressure and/or the positive end expiratory pressure (PEEP) for the respiration. At least one input sector may be selected for different respiration parameters, especially concerning the ratio of the inspiration time to the expiration time. At least one of the respiration parameters selected via its input sector may be inversely proportional to the direction of rotation of the rotary and acknowledge switch.

The rate of setting may be limited to a preset value, corresponding to the change in the respiration parameter or parameters set over time. The first and second time thresholds may be in the range of seconds and the ratio of the first time threshold to the second time threshold may advantageously be about 1.5:10.

An essential advantage of the setting process according to the principal claim is the resulting possibility of starting a setting mode for a respiration parameter by pressing the rotary and acknowledge switch longer beyond a preset first time threshold, which mode sends the currently set value, i.e., the currently set variable of the respiration parameter, directly to the control unit for the current respiration control during an adjustment that follows in time, with the rotary and acknowledge switch being continued to be pressed. At any point in time during this setting, it is possible to change over again into the previous respiration parameter setting operation by releasing the rotary and acknowledge switch, in which case the operator will be in the previously selected state of presetting.

An exemplary embodiment of the present invention will be explained below on the basis of the only figure. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

The only FIGURE is a state diagram schematically depicting the acknowledge switch.

DESCRIPTION OF THE PREFERRED EMBODIMENTS

Figure 1:
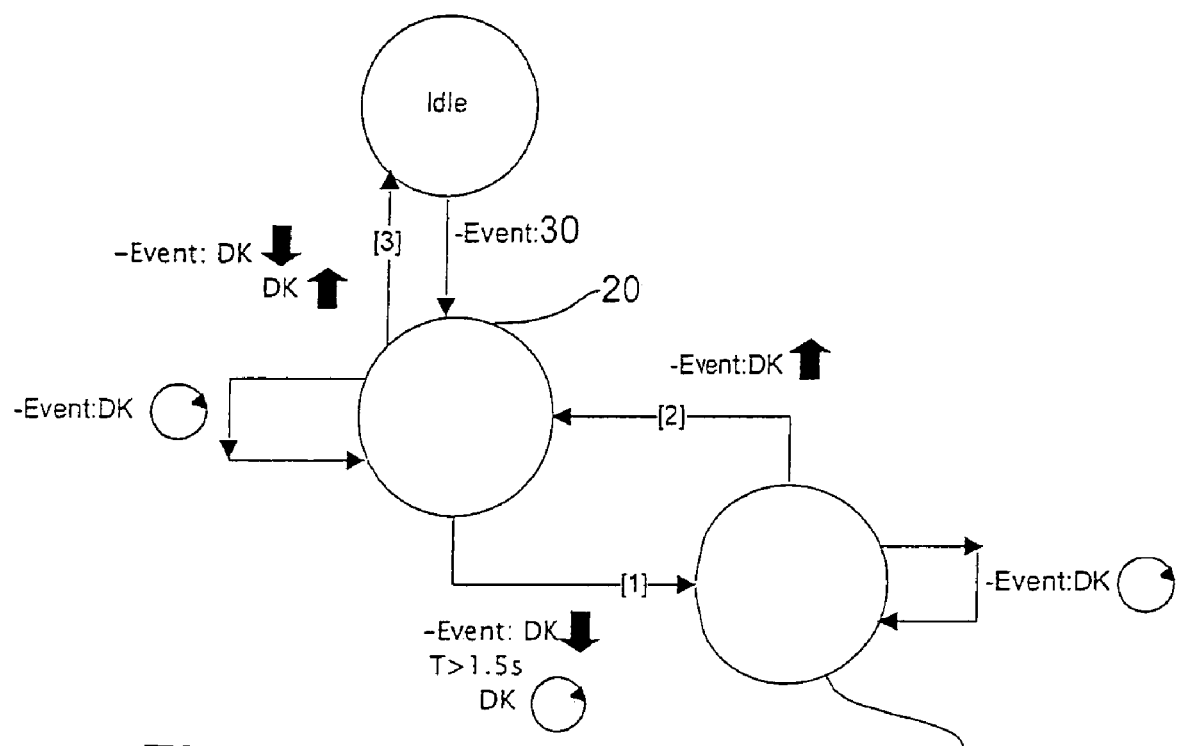

Referring to the drawings in particular, The process is described by means of the rotary and acknowledge switch "DK" shown schematically. In a so-called "recruitment" manoeuver, the inspiratory pressure is increased during the mechanical respiration in a few breathing strokes and then reduced again immediately. Closed areas of the lungs are sought to be opened by this inflation of the lungs. It is advantageous during this manoeuver to be able to respond rapidly to the patient's situation. This becomes possible through the following procedure:

After selecting the respiration parameter "inspiratory pressure" ($P_{insp}$) corresponding to "Event: 30" in the figure, it is possible at any point in time to change over into the new setting mode 10 by pressing the rotary and acknowledge switch "DK" (black arrow points downward) and keeping it pressed beyond a first preset time threshold of, e.g., 1.5 sec, which is stored in the control unit, according to step 1. The first setting mode 10 makes it possible to increase or decrease the value of the selected parameter corresponding to the direction of rotation by means of the rotary and acknowledge switch DK and the control unit, which is switched to functional connection therewith. An adjustment corresponding to the direction of rotation leads directly to an increase or decrease in pressure according to the direction of rotation via the respiration control. By releasing the rotary and acknowledge switch (black arrow points upward), a changeover into the presetting mode 20 is effected according to step 2. Pressing the rotary and acknowledge switch and keeping it pressed within a second preset time threshold of, e.g., 10 sec after the rotary and acknowledge switch was released, which time threshold is stored in the control unit, immediately leads to the new setting mode 10 with the increased or decreased set value for the selected respiration parameter. With this it is possible to manipulate the rotary and acknowledge switch without problems for the further adjustment corresponding to the selected direction of rotation. The setting operation is terminated by simply pressing and releasing the rotary and acknowledge switch at step 3 within the first preset time threshold in the presetting mode 20 when no rotation has taken place. The rate of setting is preferably limited during the adjustment in the new setting mode 10 in order not to set accidentally excessively great increments. For example, the rate of setting is limited, for example, to 10 mbar per sec for the inspiratory pressure. If a preset, optional confirmation limit for the active respiration parameter is reached in the new setting mode 10, this is acknowledged by changing over first into the old setting mode 20 and subsequently, without further rotation, again into the new setting mode 10. If the confirmation limit is acknowledged, further adjustment is possible beyond this. Besides for the inspiratory pressure, the process may also be used for other respiration parameters, optionally also in combination, for example, for the inspiration time and the expiration time during the respiration.

Other respiration parameters, which can preferably be set either individually or in combination according to this process, are the positive end expiratory pressure (PEEP), the inspiration time and/or the respiration rate, besides the inspiratory pressure.

While specific embodiments of the invention have been shown and described in detail to illustrate the application of the principles of the invention, it will be understood that the invention may be embodied otherwise without departing from such principles.

What is claimed is:

1. A process for setting an anesthesia apparatus or respirator by means of an input unit for the input of commands into a control unit controlling respiration, wherein the input unit is combined with a display unit and wherein the input unit has a keyboard for activating preselected input sectors as well as associated output sectors for respiration parameters and a corresponding value of the parameters, and the input unit is provided with a combined rotary and acknowledge switch, which is in functional connection with the input sectors, the process comprising the steps of:
   a) after selecting an input sector for a respiration parameter with the input unit, pressing the rotary and acknowledge switch and keeping the rotary and acknowledge switch pressed beyond a preset first time threshold and subsequently adjusting the respiration parameter starting from a presetting value to a new value corresponding to a direction of rotation of the rotary and acknowledge switch, an increase or decrease of the value of the selected parameter from the presetting value to the new value being directly brought about via the control unit;
   b) changing over of the new value of the selected parameter into the presetting value by releasing the rotary and acknowledge switch;
   c) a renewed pressing of the rotary and acknowledge switch and keeping the rotary and acknowledge switch pressed within a second, preset time threshold, after releasing the rotary and acknowledge switch according to step b), leads to a setting of the parameter selected at the new value with a further increased or decreased parameter value with a further direction of rotation of the rotary and acknowledge switch, so that a further adjustment of the selected parameter setting to a further new value is possible; and
   d) following a release of the rotary and acknowledge switch following either step a) or c), pressing and releasing the rotary and acknowledge switch within the first time threshold after one of the steps a) or b) brings about confirmation of the adjustment of the parameter to either the new value or the further new value.

2. A process in accordance with claim 1, wherein the selected respiration parameter is an inspiratory pressure and/or a positive end expiratory pressure (PEEP) for the respiration.

3. A process in accordance with claim 1, wherein at least one input sector is selected for different respiration parameters, especially concerning a ratio of inspiration time to expiration time.

4. A process in accordance with claim 1, wherein at least one of the respiration parameters selected via its input sector is inversely proportional to the direction of rotation of the rotary and acknowledge switch.

5. A process in accordance with claim 1, wherein a rate of setting is limited to a preset value, corresponding to the change in the respiration parameter or parameters set over time.

6. A process in accordance with claim 1, wherein the first and second time thresholds are in the range of seconds and that a ratio of the first time threshold to the second time threshold is about 1.5:10.

7. A process for setting an anesthesia apparatus or respirator, the process comprising the steps of:
   providing an input unit for the input of commands into a control unit controlling respiration, wherein the input unit is combined with a display unit and wherein the input unit has a keyboard for activating preselected input sectors as well as associated output sectors for respiration parameters and a corresponding value of the parameters, and the input unit is provided with a combined rotary and acknowledge switch, which is in functional connection with the input sectors;

selecting an input sector for a respiration parameter, the respiration parameter having a presetting value;

subsequent to said step of selecting, pressing the rotary and acknowledge switch and keeping it pressed beyond a preset first time threshold;

rotating said rotary and acknowledge switch during said pressing to directly change the actual value or the parameter, via the control unit, from a presetting value to a new value corresponding to a direction of rotation of the rotary and acknowledge switch;

releasing the rotary and acknowledge switch such that a change-over of the actual value or the parameter from the new value back into the presetting value occurs;

making a renewed pressing of the rotary and acknowledge switch and keeping it pressed within a second, preset time threshold after said step of releasing the rotary and acknowledge switch to return to the new value;

further rotating the rotary and acknowledge switch during said step of renewed pressing to set the parameter selected with an increased or decreased value from the new value, so that a further adjustment of the selected parameter setting is possible from the new value to another new value; and pressing the rotary and acknowledge switch and keeping it pressed within a first time threshold after said step of releasing the rotary and acknowledge switch or after said step of further rotating the rotary and acknowledge switch to bring about a confirmation of a set parameter setting at the new value or at the further new value.

8. A process in accordance with claim 7, wherein the selected respiration parameter is an inspiratory pressure and/or a positive end expiratory pressure (PEEP) for the respiration.

9. A process in accordance with claim 7, wherein at least one input sector is selected for different respiration parameters, especially concerning a ratio of inspiration time to expiration time.

10. A process in accordance with claim 7, wherein at least one of the respiration parameters selected via its input sector is inversely proportional to the direction of rotation of the rotary and acknowledge switch.

11. A process in accordance with claim 7, wherein a rate of setting is limited to apreset value, corresponding to the change in the respiration parameter or parameters set over time.

12. A process in accordance with claim 7, wherein the first and second time thresholds are in the range of seconds and that a ratio of the first time threshold to the second time threshold is about 1.5:10.

13. A process for setting an anesthesia apparatus or respirator, the process comprising:

providing an input unit for the input of commands into a control unit controlling respiration, wherein the input unit is combined with a display unit and wherein the input unit has a keyboard for activating preselected input sectors as well as associated output sectors for respiration parameters and a corresponding value of the parameters, and the input unit is provided with a combined rotary and acknowledge switch, which is in functional connection with the input sectors;

selecting an input sector for a respiration parameter;

pressing the rotary and acknowledge switch and keeping it pressed for an initial pressing preset time period;

rotating the rotary and acknowledge switch during pressing to change the value of the parameter from a presetting value to a new value corresponding to a direction of rotation of the rotary and acknowledge switch;

releasing the rotary and acknowledge switch to change the value of the parameter from the new value back to the presetting value;

follow up pressing the rotary and acknowledge switch within a follow up preset time period after the step of releasing the rotary and acknowledge switch to change a value of the parameter from the presetting value back to the new value;

during the follow up pressing, rotating the rotary and acknowledge switch to adjust the value or the parameter corresponding to the direction of rotation of the rotary and acknowledge switch from the new value to a further new value;

pressing and releasing the rotary and acknowledge switch within an acknowledge preset time period after the step of releasing the rotary and acknowledge switch or within the acknowledge preset time period after releasing the rotary switch to end said follow up pressing to bring about a confirmation of the value of the parameter at the new value or at the further new value.

14. A process in accordance with claim 13, wherein said acknowledge preset time period is substantially the same as said initial pressing preset time period.

15. A process in accordance with claim 13, wherein the selected respiration parameter is an inspiratory pressure and/or a positive end expiratory pressure (PEEP) for the respiration.

16. A process in accordance with claim 13, wherein at least one input sector is selected for different respiration parameters, especially concerning a ratio of inspiration time to expiration time.

17. A process in accordance with claim 13, wherein at least one of the respiration parameters selected via its input sector is inversely proportional to the direction of rotation of the rotary and acknowledge switch.

18. A process in accordance with claim 13, wherein a rate of setting is limited to a preset value, corresponding to the change in the respiration parameter or parameters set over time.

19. A process in accordance with claim 13, wherein said acknowledge preset time period and said initial pressing preset time period are both a first preset time period;

said follow up preset time period is a second preset time period;

said first preset time period and said second preset time period are in a range of seconds; and a ratio of said first preset time period to said second preset time period is about 1.5:10.

* * * * *